United States Patent [19]

Webster et al.

[11] Patent Number: 4,584,879
[45] Date of Patent: Apr. 29, 1986

[54] COMPONENT INSPECTION BY SELF GENERATED TRANSIENT STRESS WAVE DETECTION

[75] Inventors: John R. Webster; Trevor J. Holroyd, both of Mickleover, England

[73] Assignee: Rolls-Royce Limited, London, England

[21] Appl. No.: 621,729

[22] Filed: Jun. 18, 1984

[30] Foreign Application Priority Data

Aug. 10, 1983 [GB] United Kingdom ................ 8321479

[51] Int. Cl.³ ............................................ G01N 29/04
[52] U.S. Cl. .................................................. 73/588
[58] Field of Search ................................. 73/588, 582

[56] References Cited

U.S. PATENT DOCUMENTS

| | | | |
|---|---|---|---|
| 3,564,903 | 2/1971 | Woodmansee et al. | 73/582 |
| 4,111,053 | 9/1978 | Geithman et al. | 73/588 |
| 4,122,724 | 10/1978 | Geithman et al. | 73/588 |

Primary Examiner—Stephen A. Kreitman
Attorney, Agent, or Firm—Cushman, Darby & Cushman

[57] ABSTRACT

A method of inspecting a component in which the surface of the component is scanned with a loud speaker, the sonic output of which is arranged to be at such a frequency or frequencies as to cause any cracks, fractures or unbonded regions within the component to generate transient stress wave emissions. An acoustic emission transducer is attached to the component surface so as to detect any such transient stress wave emissions and thereby provide evidence of the existence of any such cracks, fractures or unbonded regions.

6 Claims, 2 Drawing Figures

4,584,879

COMPONENT INSPECTION BY SELF GENERATED TRANSIENT STRESS WAVE DETECTION

BACKGROUND OF THE INVENTION

This invention relates to the inspection of components by self generated transient stress wave detection.

If certain components are tapped or otherwise mechanically excited in order to cause them to vibrate, they generate acoustic emissions which are peculiar to the components concerned. Variations in the acoustic emissions of components which are generally similar do arise however if a component has a fault, such as a crack, within it. This being so, it is possible to identify faulty components by determining their acoustic emissions when excited and comparing those acoustic emissions with the acoustic emissions from a component which is known not to be faulty.

A drawback with this technique is that although it is effective in detecting faults in components, it is difficult to determine their location and extent. Usually other techniques such as X-ray photography or ultrasonic inspection have to be employed in order to obtain this information. X-ray photography carries potential health hazards and both X-ray photography and ultrasonic inspection are difficult to use on certain components which have to be inspected whilst they are located on other components.

A further drawback is that the means which is used to mechanically excite the component may itself generate acoustic emissions which could mask the acoustic emissions which are generated within the component. Such acoustic emissions could for instance be generated by fretting between the component and the exciter means.

One example of a component, the inspection of which introduces these difficulties, is a ducted fan gas turbine engine fan blade which is either of laminated construction or is made up of a metal skin surrounding a core of a suitable lightweight material. In both modes of construction, the fan blades have to be inspected in order to detect any bonding effects between the laminates or between the core and the skin. Since these defects can arise during engine operation, it is necessary to have some form of inspection technique which can be employed whilst the fan blades are located on the engine. X-ray photography and ultrasonic inspection are not easily amenable to this form of inspection.

It is an object of the present invention to provide a method of inspecting a component for defects which method may be used in locations in which the use of alternative methods of inspection is inconvenient or even impossible, and which, in certain embodiments, is capable of determining the location of those defects.

SHORT STATEMENT OF THE INVENTION

According to the present invention, a method of inspecting a component comprises exposing the surface of said component to the sonic output of sonic transmission means which sonic output is at such a frequency or frequencies as to cause any adjacent abutting surfaces within said component to move relative to each other and thereby generate transient broadband stress vanes and providing detection means to detect any such generated transient broadband stress vanes to provide evidence of the existence of any such adjacent abutting surfaces.

BRIEF DESCRIPTION OF THE DRAWINGS

The invention will now be described, by way of example, with reference to the accompanying drawings in which.

DETAILED DESCRIPTION OF THE PREFERRED EMBODIMENT

Figure 1:
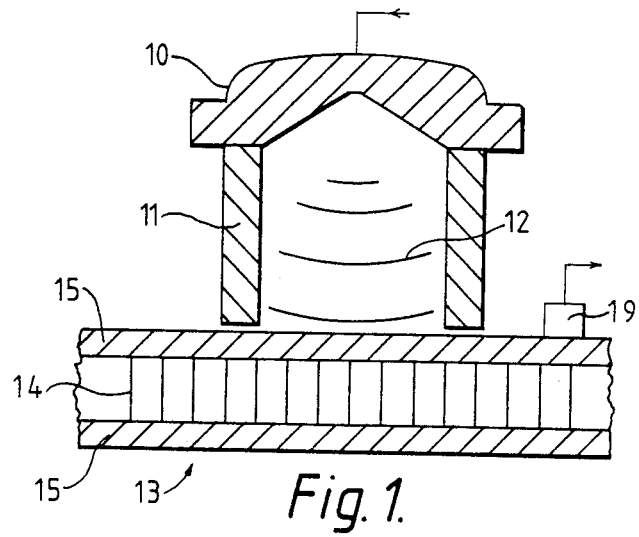
FIG. 1 is a sectioned side view of inspection apparatus being used in accordance with the method of the present invention.

With reference to FIG. 1, a high frequency output loudspeaker 10, which is of the type generally known as a "tweeter", is provided with a circular cross-section guide 11. The guide 11 ensures that the sonic output 12 of the loudspeaker 10 is directional and impinges upon a laminated honeycomb structure 13 which is to be inspected and which is situated adjacent the guide 11.

The laminated honeycomb structure 13 is constituted by an open-celled honeycomb material 14 is bonded to, and sandwiched between two impervious sheets 15. In this particular case, the laminated honeycomb structure 13 is a part of a fan blade for a ducted fan gas turbine propulsion engine. However the method of the present invention is not limited to the inspection of such laminated honeycomb structures. Thus mention may be made of components having thin walls such as aircraft skins, missiles, storage tanks, solar panels etc. Moreover the components need not be metallic and could be in fact formed from composite materials such as fibre-reinforced plastics which may or may not be laminated.

Figure 2:
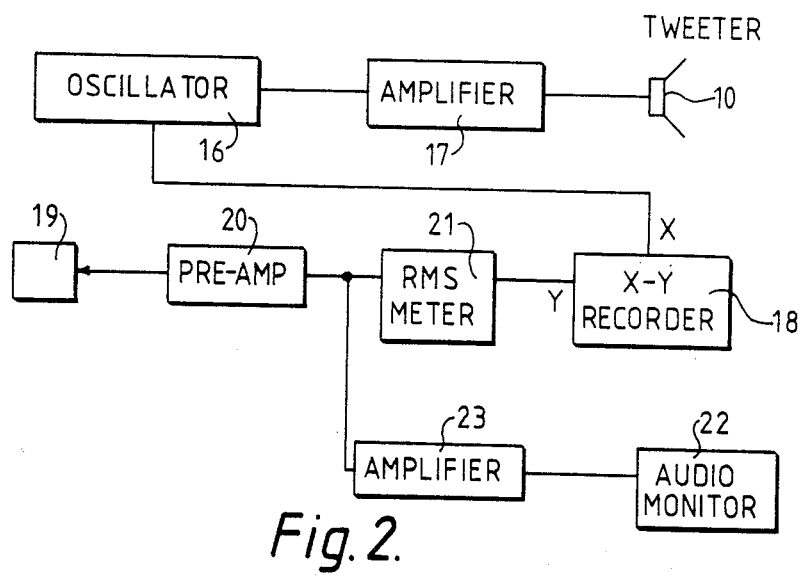
FIG. 2 is a block diagram of circuitry suitable for use with the inspection apparatus shown in FIG. 1.

The loudspeaker 20, as can be seen from the block diagram of FIG. 2, is driven by an oscillator 16 and amplifier 17. The oscillator 16 also drives an X-Y recorder 18 which is in turn also driven by an acoustic emission transducer 19 via a pre-amplifier 20 and a root mean square meter 21. The pre-amplifier 20 also drives an audio monitor 22 via an amplifier 23.

The acoustic emission transducer 19 is attached to the surface of the laminated honeycomb structure 13 as can be seen in FIG. 1. Its purpose is to detect any self generated transient broadband stress waves which emanate from within the laminated honeycomb structure 13. Such emissions arise from relative movement between adjacent abutting surfaces within the laminated honeycomb structure 13 caused by the sonic output 12 from the loudspeaker 10.

In operation, the loudspeaker 10 is positioned over the area of the laminated honeycomb structure 13 under investigation and the oscillator 16 is activated to provide a sinusoidal output of steadily increasing frequency of, for instance, 5 KHz to 25 KHz. The output is fed to the X-Y recorder 18 as well as to the loudspeaker 10 via the amplifier 17.

The output from the loudspeaker 10 acts upon any adjacent abutting surfaces within the laminated honeycomb structure 13 so that at certain vibrational frequencies those adjacent abutting surfaces move relative to each other to provide self generated transient board band stress waves. These transient stress wave emissions are detected by the acoustic emission transducer 19 which provides a output which is representative of those emissions. That output is fed to the pre-amplifier 20 which in turn provides an output which is divided between the amplifier 23 and the root mean square meter 21. The amplifier 23 provides an output to the audio monitor 22 which serves to give an audible indication of the output of the acoustic emission transducer 19. The root mean square meter 21 converts the output from the acoustic emission transducer 19 into a form which is suitable for the input of the X-Y recorder 18. The X-Y recorder thus provides a plot of emissions from the laminated honeycomb structure 13 verses the frequencies from the loudspeaker 10 which give rise to those transient stress wave emissions.

The transient stress wave emissions from the laminated honeycomb structure 13 are dependent upon the integrity of that structure and in particular are dependent upon whether there are any adjacent abutting surfaces such as those provided by cracks or fractures in the structure or regions in which there is incomplete bonding between the honeycomb material 14 and the sheets 15. Thus the transient stress wave emissions from sound laminated honeycomb structures 13 differ from those from unsound structures 13. It is generally the same that these differences are more readily apparent at certain output frequencies of the loudspeaker 10 than they are of other frequencies. This being so a comparison of the plots from the X-Y recorder or unsound laminated honeycomb structures 13 with the plots from sound structures 13 provides an indication of the frequencies which give rise to the greatest different in transient stress wave emissions. If a frequency which gives the greatest difference in transient stress wave emissions is then selected, the examination of subsequent samples of the laminated honeycomb structure 13 need only be carried at the chosen frequency rather than over a range of frequencies.

As described above, the method of the present invention is used to examine a single area of a laminated honeycomb structure 13. This being so, the guide 11 may be omitted in circumstances in which localised examination of the component is not necessary.

Once the optimum frequency for transient stress wave emission has been determined, the loud speaker 10 and its associated guide 11 can be used to scan the whole of the surface of a laminated honeycomb structure 13 in order to locate any localised areas of cracking, fractures or lack of bonding. This can be done by manually scanning the surface, listening to the audio monitor 22 and making a note of the areas which produce transient stress wave emissions which are at variance with those from areas which are known to be sound. An alternative to such manual operation would be to mount the loud speaker 10 and its associated guide 11 on a suitable mechanical scanning device and provide a suitable recording device in place of the audio monitor 22 in order to ensure a record of the location of unsound areas of the structure 13 under investigation. In both of these cases, although the loud speaker 10 and its associated guide 11 and moved over the surface of the component under examination, there is in fact no need to move the acoustic emission transducer 19. Generally speaking, it is capable of picking up transient stress wave emissions which are generated anywhere within the structure 13 subject of course to the structure not being so large that the transient stress wave emissions are insufficiently strong to reach the transducer 19.

The method of the present invention thus provides a rapid and convenient method of examining components in situ without the requirement for elaborate and expensive X-ray photography and ultrasonic equipment. This is particularly useful in the examination of gas turbine engine fan blades since these can be readily examined for structural faults without their removal from the engine or the removal of the engine from the aircraft on which they are mounted. As previously stated however, the invention is not limited to such use and could be used in the inspection of other components which may include adjacent abutting surfaces. Thus mention may be made of components which include cracks, fractures, unbonded and loose joints, delaminations and loose rivets or other fasteners.

We claim:

1. A method of inspecting a component comprising the steps of:

exposing the surface of said component to the sonic output of a sonic transmission means, said sonic output being at at least one frequency from causing adjacent abutting surfaces within said component to move relative to one another, said moving surfaces generating transient broadband stress waves; and detecting said generated transient broadband stress waves to provide evidence of the existence of any such moving adjacent abutting surfaces.

2. A method of inspecting a component as defined in claim 1, comprising the step of adapting said sonic transmission means to generate a directional sonic output so that only adjacent abutting surfaces in a direction of sonic transmission are excited by said sonic transmission.

3. A method of inspecting a component as defined in claim 2, further comprising the step of scanning said sonic transmission means over the surface of said component so as to detect moving adjacent abutting surfaces within said component over said component.

4. A method of inspecting a component as defined in claim 1, wherein said sonic transmission means is a loudspeaker positioned adjacent the surface of said component.

5. A method of inspecting a component as defined in claim 1, wherein said detection means for detecting said transient broadband stress waves is an acoustic emission transducer attached to the surface of said component.

6. A method of comprising a component as defined in claim 1, wherein said component is a laminated honeycomb structure comprising an open celled honeycomb material which is bonded to and sandwiched between two sheets of impervious material.

* * * * *